US011344228B2

(12) United States Patent
Ovalle et al.

(10) Patent No.: US 11,344,228 B2
(45) Date of Patent: May 31, 2022

(54) PATIENT MONITORING DEVICE AND SYSTEM

(71) Applicants: Wernher Ovalle, Costa Mesa, CA (US); Brian Ross, Costa Mesa, CA (US)

(72) Inventors: Wernher Ovalle, Costa Mesa, CA (US); Brian Ross, Costa Mesa, CA (US)

( * ) Notice: Subject to any disclaimer, the term of this patent is extended or adjusted under 35 U.S.C. 154(b) by 471 days.

(21) Appl. No.: 16/402,183

(22) Filed: May 2, 2019

(65) Prior Publication Data

US 2020/0077925 A1 Mar. 12, 2020

Related U.S. Application Data

(60) Provisional application No. 62/665,815, filed on May 2, 2018.

(51) Int. Cl.
*A61B 5/00* (2006.01)
*A61B 5/11* (2006.01)
*A61G 7/05* (2006.01)

(52) U.S. Cl.
CPC ............ *A61B 5/1115* (2013.01); *A61B 5/002* (2013.01); *A61B 5/0059* (2013.01); *A61B 5/1126* (2013.01); *A61B 5/742* (2013.01); *A61B 5/7405* (2013.01); *A61B 5/746* (2013.01); *A61B 5/7465* (2013.01); *A61G 7/0524* (2016.11); *A61B 2562/0233* (2013.01)

(58) Field of Classification Search
CPC ..... A61B 5/1115; A61B 5/002; A61B 5/0059; A61B 5/1126; A61B 5/7405; A61B 5/742; A61B 5/746; A61B 5/7465; A61B 2562/0233; A61B 5/6891; A61G 7/0524; A61G 7/053
USPC ...................................... 600/587, 595; 5/424
See application file for complete search history.

(56) References Cited

U.S. PATENT DOCUMENTS

| | | | |
|---|---|---|---|
| 7,805,784 B2* | 10/2010 | Lemire | A61G 7/0509 5/611 |
| 8,258,944 B2* | 9/2012 | Riley | B60B 33/0049 340/540 |
| 10,406,045 B2* | 9/2019 | Hayes | B60K 31/0008 |
| 10,517,784 B2* | 12/2019 | Zerhusen | A61G 7/05769 |
| 2006/0279427 A1* | 12/2006 | Becker | G16H 40/20 340/573.4 |
| 2007/0157385 A1* | 7/2007 | Lemire | A61G 7/0509 5/600 |
| 2008/0083065 A1* | 4/2008 | Bautovich | A61B 5/1115 5/424 |
| 2011/0021925 A1* | 1/2011 | Wood | E05B 73/00 600/476 |
| 2013/0204098 A1* | 8/2013 | Chamney | A61B 5/70 600/301 |
| 2014/0076644 A1* | 3/2014 | Derenne | A61G 1/0287 180/19.2 |
| 2015/0061873 A1* | 3/2015 | Hyde | A61B 5/746 340/573.1 |

(Continued)

*Primary Examiner* — May A Abouelela
(74) *Attorney, Agent, or Firm* — One LLP

(57) ABSTRACT

Systems and methods for a bedside handle system having two-stage laser motion detection and wireless communication alert. The system detects and sends wireless alerts when a patient sits up and when the patient stands up. The system further includes a mobile app for receiving and displaying the alerts.

12 Claims, 10 Drawing Sheets

(56) References Cited

U.S. PATENT DOCUMENTS

| | | | |
|---|---|---|---|
| 2015/0109442 A1* | 4/2015 | Derenne | G16H 40/67 |
| | | | 348/143 |
| 2016/0078740 A1* | 3/2016 | Pirio | A61B 5/1115 |
| | | | 340/573.4 |
| 2017/0020756 A1* | 1/2017 | Hillenbrand, II | A61G 7/057 |
| 2017/0150929 A1* | 6/2017 | San | A61B 5/742 |
| 2017/0172827 A1* | 6/2017 | Schaaf | A61G 7/018 |
| 2017/0173262 A1* | 6/2017 | Veltz | A61B 5/0022 |
| 2017/0325683 A1* | 11/2017 | Larson | A61B 5/447 |
| 2018/0020841 A1* | 1/2018 | Mitsuzuka | A47C 31/00 |
| | | | 5/737 |
| 2018/0206793 A1* | 7/2018 | Akatsu | A61B 5/1121 |
| 2019/0175103 A1* | 6/2019 | Kogure | A61B 5/6892 |
| 2019/0298229 A1* | 10/2019 | Kostic | A61G 7/015 |
| 2020/0121530 A1* | 4/2020 | Akatsu | A61B 5/6891 |
| 2020/0253547 A1* | 8/2020 | Harris | A61B 5/7465 |
| 2021/0007629 A1* | 1/2021 | Todoroki | A61B 5/7246 |
| 2021/0038146 A1* | 2/2021 | Todoroki | A61B 5/6891 |
| 2021/0045699 A1* | 2/2021 | Kuwahara | A61B 5/0004 |

* cited by examiner

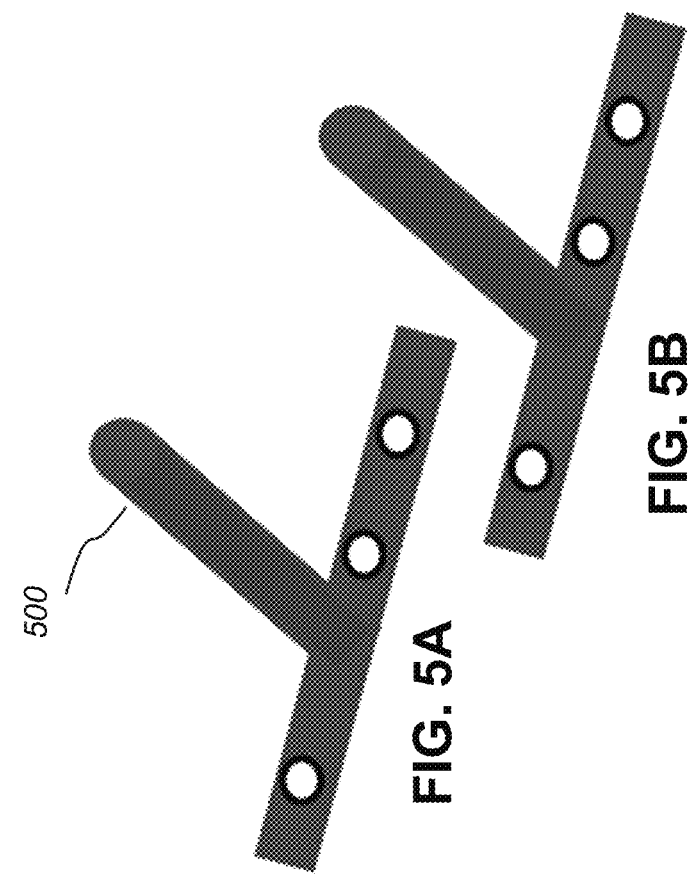
FIG. 5A
FIG. 5B
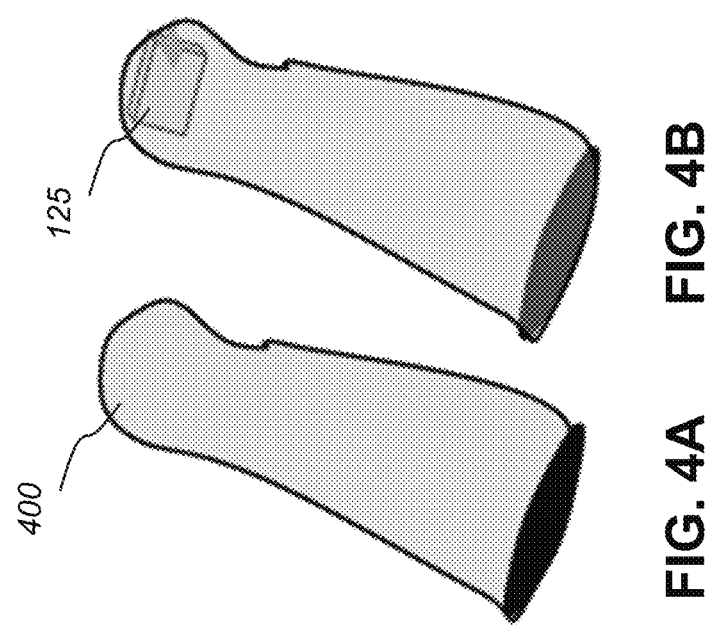
FIG. 4A
FIG. 4B

PATIENT MONITORING DEVICE AND SYSTEM

CROSS REFERENCE TO RELATED APPLICATIONS

This application claims priority pursuant to 35 U.S.C. § 119(e) to U.S. Provisional Patent Application No. 62/665,815, filed May 2, 2018 and titled "'GRIPSMART'—A NOVEL HOSPITAL BED HANDLE," the entire content and disclosure of which is hereby incorporated by reference.

FIELD

The subject matter described herein relates generally to systems, devices, and methods for patient monitoring. In particular, the subject matter provides a bedside handle system with patient monitoring and communication functions.

BACKGROUND

As of November 2017, nursing homes are being penalized for using traditional side rails and pressure-pad alarms, since both are considered forms of restraint by the Centers for Medicare and Medicaid Services. Since that time, facilities have been forced to completely remove side rails from their existing beds. It is not surprising that in a two-month period alone in 2018, the patient fall-rate increased in some areas by 200-300%. Moreover, when patients fall from the bed, the lack of a bedside alarms make it difficult to know when this occurs. Patients may be "down" for some time before being discovered. While it is true that patients are now more "free" to move about, the tradeoff is that they are at much higher risk of falls which commonly result in hip fractures, head trauma, and other injuries.

The traditional beds that use pressure pads and pull cords to sound alarms when "at-risk" patients arise from their bed have fallen out of favor because of the loud noise that is made upon movement. The Centers for Medicare & Medicaid (CME) guidelines state, "the use of position change alarms that are audible to the resident(s) may have the unintended consequence of inhibiting freedom of movement. For example, a resident may be afraid to move to avoid setting off the alarm and creating noise that is a nuisance to the resident(s) and staff or is embarrassing to the resident. For this resident, a position change alarm may have the potential effect of a physical restraint."

Thus, needs exist for systems, devices and methods for a bedside handle system with patient monitoring and communication functions that complies with regulations but without the above mentioned and other disadvantages.

SUMMARY

Provided herein are example embodiments of systems, devices and methods for providing a bedside handle system with patient monitoring and communication functions. Generally, the present disclosure may include a handle system that can be attached to patient beds, for example, beds used in skilled nursing and hospital facilities. The handle system may safely prevent patients from rolling out of bed and may be used as an assistive support for patients getting out of bed, thereby enhancing their freedom of movement. In some embodiments, the handle system may replace traditional side rails. In some embodiments, the handle system may utilize laser technology built into the handles to remotely notify staff via wireless communication capable devices when a patient has sat up, and/or stood up from the bed.

In some embodiments, the handle system may further include a large, easy-to-activate call button, located on the handles to either side, or both sides, of the bed, for patients to request staff assistance.

In some embodiments, the handle system includes a multiple-stage motion detection (patient sitting up, patient standing up) and wireless alert. In some embodiments, the bedside handle system comprises: a first handle attached to a first side rail of a patient bed, the first handle comprises a first laser beam transmitter configured to transmit a first laser beam; a second handle attached to a second side rail of the patient bed, the second handle comprises a first laser beam receiver configured to receive the first laser beam; a second laser beam transmitter attached to a first side of the patient bed and configured to transmit a second laser beam; a second laser beam receiver attached to the first side of the patient bed and configured to receive the second laser beam; a third laser beam transmitter attached to a second side of the patient bed and configured to transmit a third laser beam; a third laser beam receiver attached to the second side of the patient bed and configured to receive the third laser beam; a first call button built into the first handle; a wireless communication device attached to the patient bed and configured to receive signal from the first, second and third laser beam receivers; and wherein the wireless communication device is further configured to transmit an alert signal when one of the first laser beam, the second laser beam and the third laser beam is interrupted.

In some embodiments, the handle system may further include a software application (or "app") that provides for practical applications to the fields of patient monitoring and management, and for improvements over prior modes in these fields. The app may allow for nursing staff to individualize the level of surveillance for any given patient, and at differing times. The app may also allow for valuable analytics to further assist a facility. Further improvements can include, for example, optimization of computer resources, improved data accuracy and improved data integrity, to name only a few. In a number of embodiments, instructions stored in the memory of computing devices (e.g., software) can cause one or more processors of the handle system to perform the steps of the embodiments.

Examples of patient monitoring and management functions may include ability for facilities to manage which patients to be monitored, how alarm notices to be transmitted (e.g., to individual staff smart phones, or nursing station tablet, etc.), history of patient calls and alarms, etc. In some embodiments, the app may further include sophisticated dashboards and user interfaces. The app may be a mobile app.

In some embodiments, the handle system may further include two-way communication, for example, a computing device with at least a speaker, a microphone and a video screen. The patient may, for example, communicate with a local nursing staff, a remotely located healthcare personnel, or a remotely located family member or friends.

In some embodiments, the handle system may further include validating data that it generates or acquires. For example, patient data may be validated for accuracy or error-free before use.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Moreover, it is noted that the invention is not limited to the specific embodiments described in the Detailed Description and/or other sections of this document. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated in and constitute a part of the specification, are for illustrative purposes only of selected embodiments, serve to explain the principles of the invention. These drawings do not describe all possible implementations and are not intended to limit the scope of the present disclosure.

FIGS. 4A to 5B show an example of the parts of the handle of the bedside handle system, according to various embodiments of the present disclosure.

DETAILED DESCRIPTION

Figure 1A:
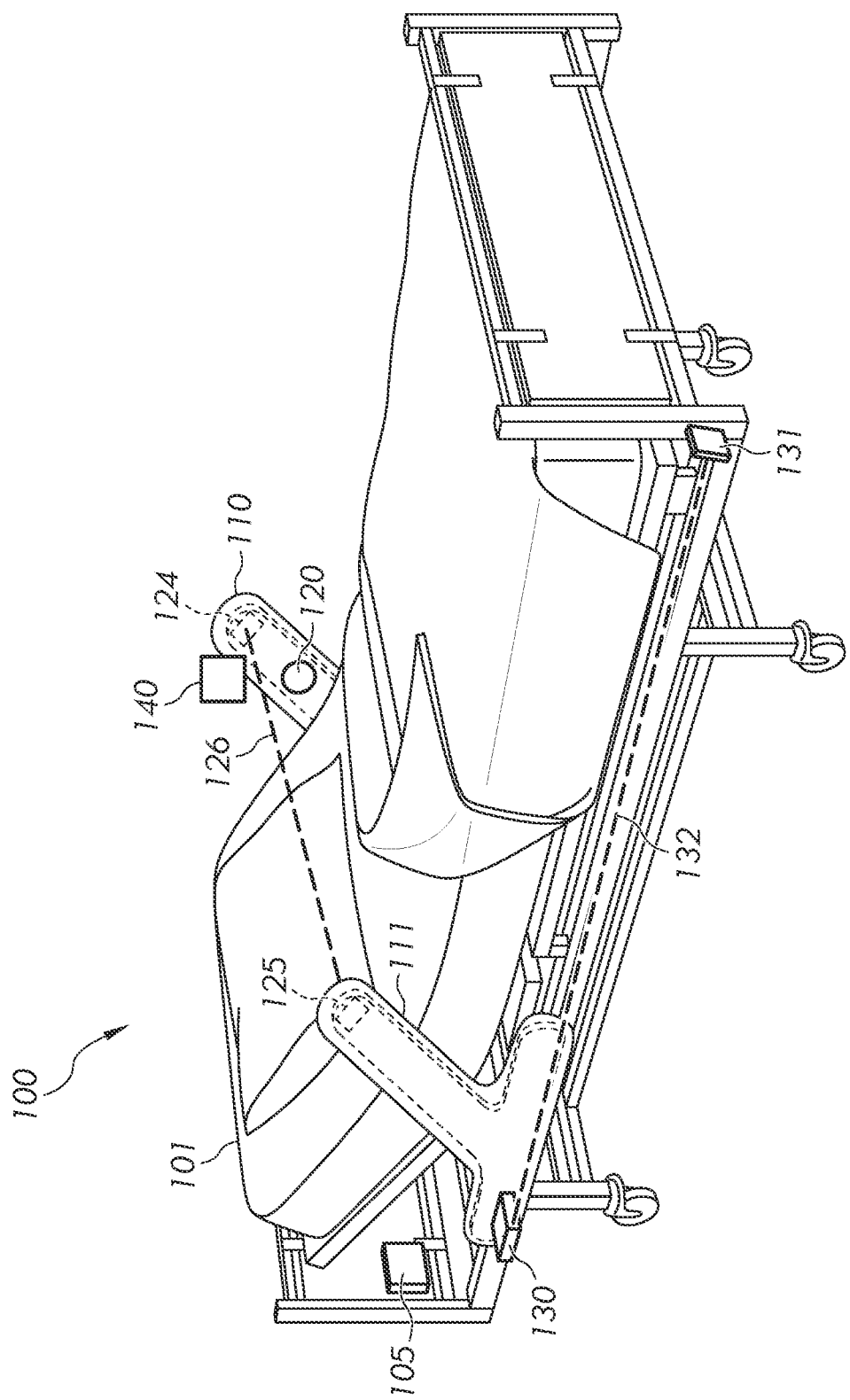
FIGS. 1A and 1B show an exemplary bedside handle system for a patient bed, according to various embodiments of the present disclosure.

The present disclosure relates to systems and methods for a bedside handle system with patient monitoring and communication functions.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

In some embodiments, the bedside handle system may retro-fit to existing hospital and nursing home bed or integrate in new bed design. The bedside handle system may be attached (e.g., bolted) onto the bed frame. The bedside handle system may prevent patients from rolling off the bed and improve the patient's ability to get out of bed since she can use it for support. The bedside handle system may include motion detection devices using laser technology to identify when a patient has sat up, and/or when a patient has stood up. The bedside handle system may further include communication capability to send alarm information to one or more remote devices. In some embodiments, the communication may use wireless technology, e.g., Wi-Fi technology. The remote device may be a smart device (e.g., smart phone) or a tablet computing device, a laptop, or a wearable computing device. The bedside handle system may further include an App that provides an interactive dashboard to easily manage patients. For example, a nursing staff may have the option to select or configure which patients need to be monitored, sit-alarms, stand-alarms, or both, time of operation (e.g., day, night, or through 24-hour periods).

In some embodiments, an alarm notification may be sent to a general pool, or individualized to one or more designated persons (e.g., a certified nurse assistant (CNA), or a registered nurse (RN)), in which case the signal would be sent directly to their respective smart device. In some embodiments, data available through the app may include response times, individual staff performance, detailed fall risk assessments and suggested action items.

In some embodiments, an alarm notification may include one or more messages. In some embodiments, the notification may also include voice messages.

In some embodiments, the bedside handle system may further include a call button located on one or both handles for patients to ask for assistance. The communication (e.g., Wi-Fi) capability will allow for that request to be sent to a targeted CNA/RN or a general pool. The bedside handle system may track time-to-patient data for each individual staff member, stations, or facility at large.

Figure 1B:
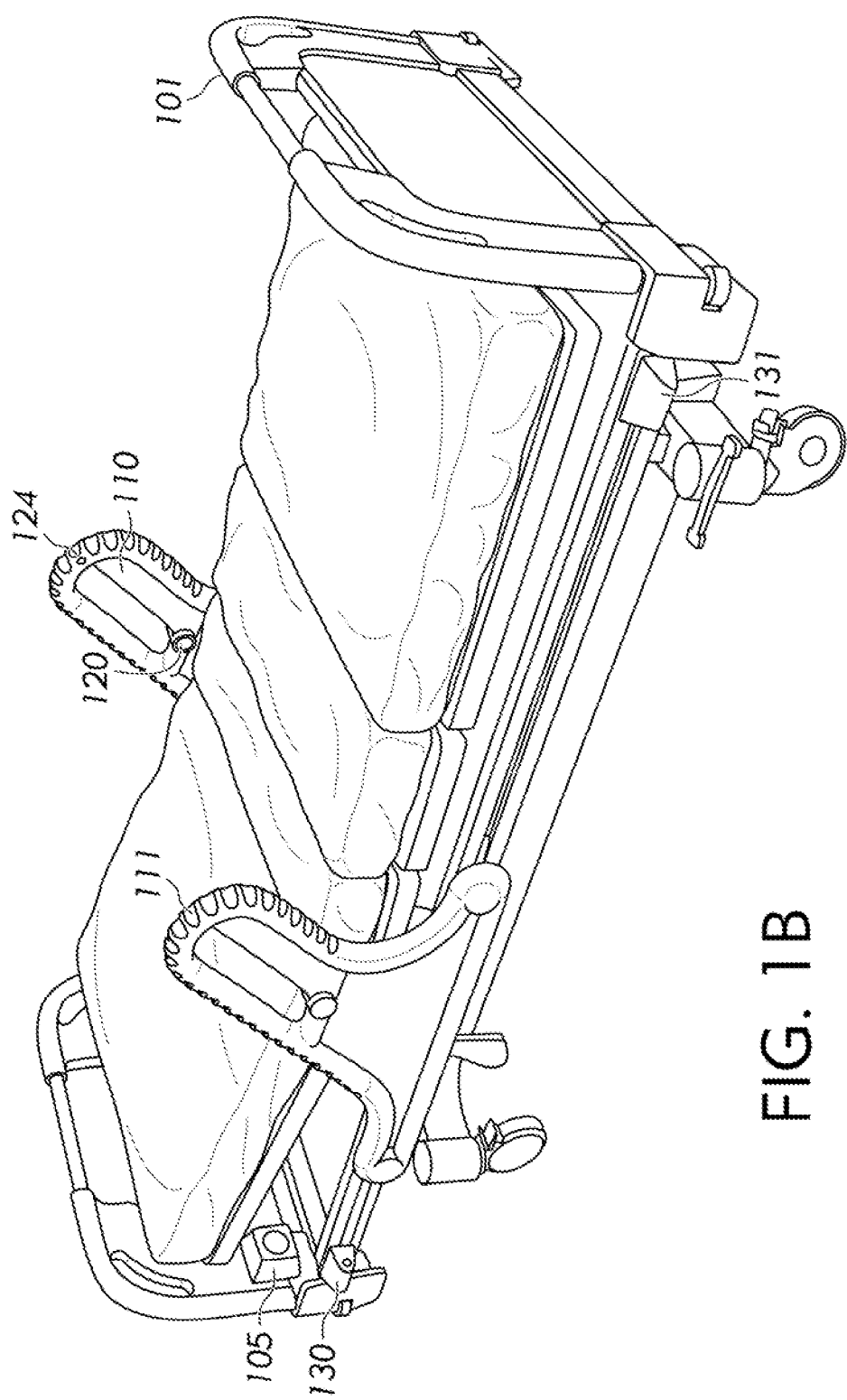

Referring now to FIGS. 1A and 1B, an exemplary embodiment of the bedside handle system 100 is shown for a patient bed 101. The bedside handle system 100 may include two arm handles 110 and 111, attached to each side of the patient bed 101. In some embodiments, the handles 110 and 111 may be attached to the first and second side rails on each side of the bed. A first built-in laser sensor transmitter 124 and receiver 125 may be positioned near the top end of (away from the side rails) of the handles 100 and 111. Laser sensor 124 and 125 emits and receives a first laser beam 126. A second built-in laser sensor transmitter 130 and receiver 131 may be positioned along the first side of the bed, one near the head and one near the foot of the bed. Laser sensor 130 and 131 emits and receives a second laser beam 132. Not shown is a third built-in laser sensor transmitter and receiver positioned along the second side of the bed (opposite from the first side of the bed), one near the head and one near the foot of the bed. The third laser sensor emits and receives a third laser beam (not shown).

In some embodiments, when any of the first laser beam 126, the second laser beam 126, or the third laser beam is interrupted, a pre-determined alert is sent. The alert may be sent using a wireless communication device 105 described below. The alert indicates which laser beam has been interrupted. In some embodiments, the alert is sent without disrupting the patient room with a loud sound.

Figure 2A:
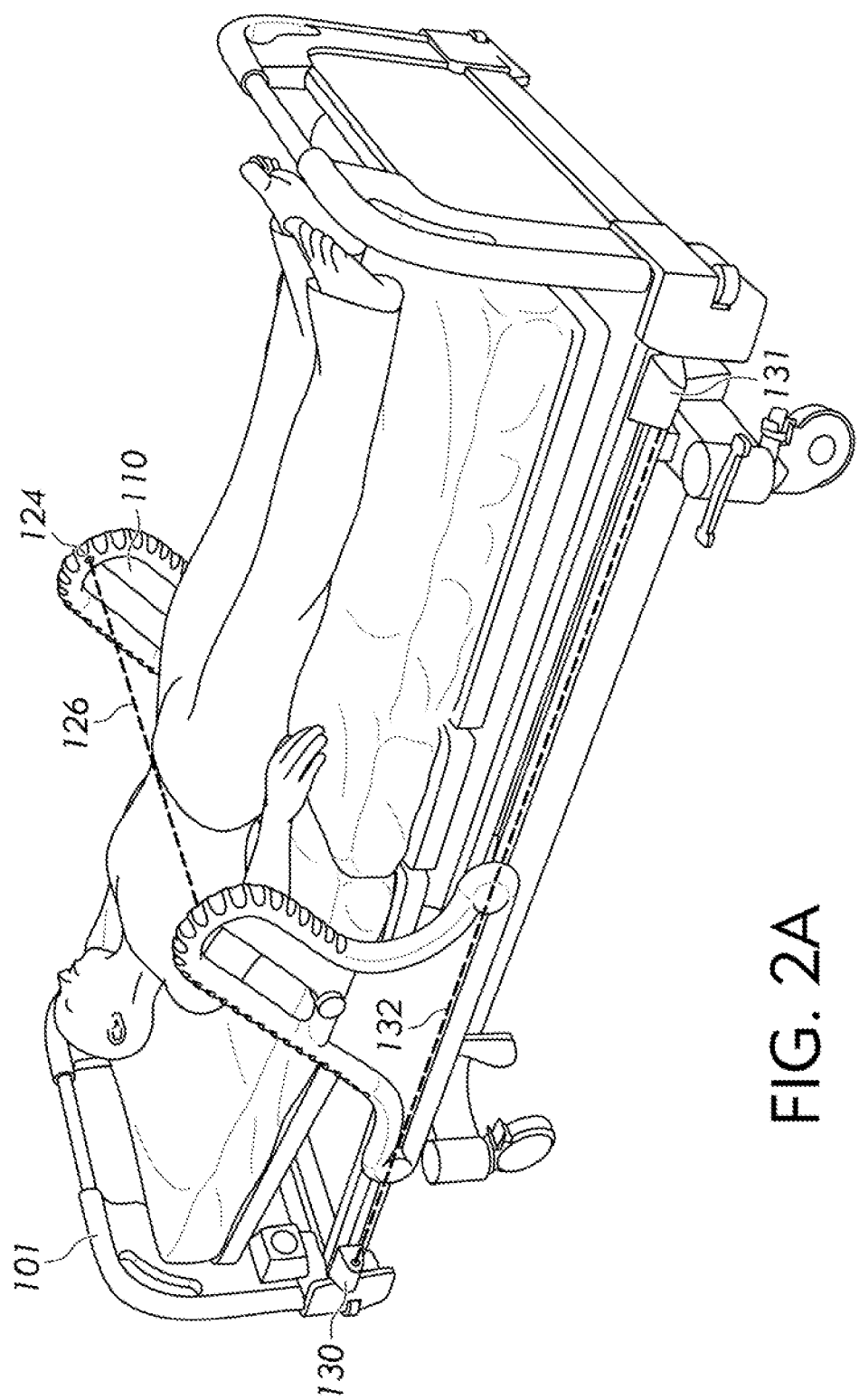
FIG. 2A shows the bedside handle system installed on the patient bed, showing patient resting, according to various embodiments of the present disclosure.
Figure 2B:
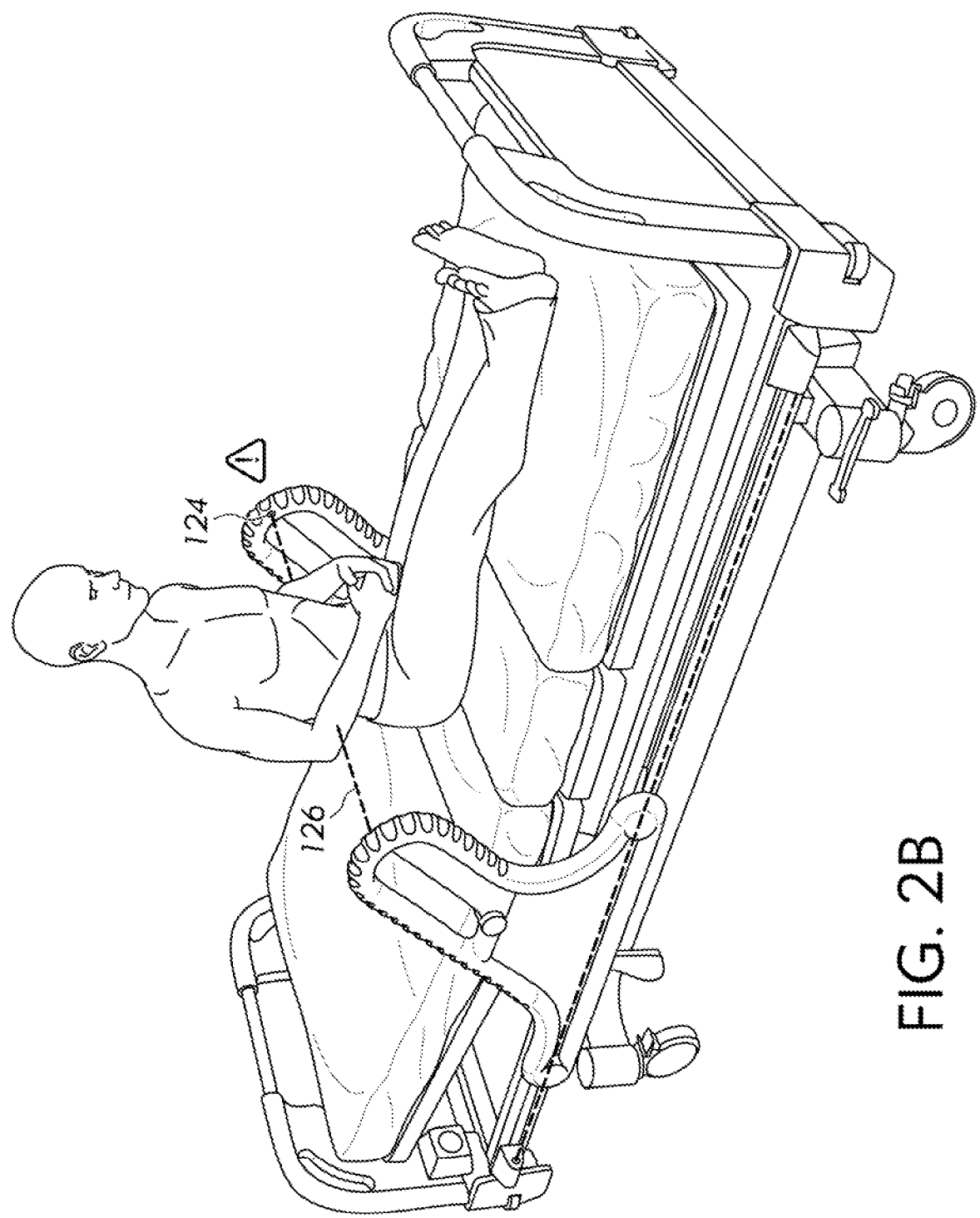
FIG. 2B shows the bedside handle system installed on the patient bed, showing patient sitting up, according to various embodiments of the present disclosure.

As advantageously positioned, when the laser beam 126 is interrupted, the bedside handle system 100 sends an alert indicating that the patient has sat up on the bed (see example in FIG. 2B). Also as advantageously positioned, when the laser beam 132, or the third laser beam is interrupted, the bedside handle system 100 sends an alert indicating that the patient has stood up from the bed, or about to stand up from the bed (see example in FIG. 2C). Alert details may indicate which side of the bed the laser beam has been interrupted.

In some embodiments, the bedside handle system 100 may use laser technology at less than 5 milliwatts, making it safe and incapable of causing eye damage. The beam will not be visible (or human perceivable). Laser technology is advantageously economical.

In some embodiments, the bedside handle system 100 may include a wireless communication device 105. The wireless communication device 105 may include electronics and interfaces for transmitting data to and receiving data from one or more remote devices. In some embodiments, the wireless communication device 105 supports Wi-Fi technology and other suitable wireless technologies.

In some embodiments, the bedside handle system 100 may further include two large call buttons 120 each built-into handle 110 and 111. The call buttons may be connected to the wireless communication device 105 for communicating, e.g., sending call signal to, a nurse station or one or more designated individuals. The call signal may cause a light to be lighted, a message to be displayed, or any other suitable signal to alert that the patient needs help or attention.

In some embodiments, the call button 120 may be connected to a nurse station using wired connection.

In some embodiments, the bedside handle system 100 may further include a two-way communication device 140 built-into either handle 110 or 111. The communication device 140 may be or may include a computing device with at least a speaker, a microphone and a video display screen. The communication device 140 may be connected to the wireless communication device 105. The patient may use the communication device 140 to communicate, for example, with a local nursing staff, a remotely located healthcare personnel, or a remotely located family member or friends, using audio alone or audio and visual (e.g., teleconference).

FIG. 2A shows an example of the bedside handle system 100 installed on the patient bed 101, showing the patient resting without interrupting first laser beam 126, second laser beam 132, or third laser beam (not shown, on other side of bed 101).

FIG. 2B shows an example of the bedside handle system 100 installed on the patient bed 101, showing the patient sitting up and interrupting first laser beam 126. The bedside handle system 100 thus sends an alert signal as described above, indicating among other details that the first laser beam 126 has been interrupted, e.g., that patient has sat up.

Figure 2C:
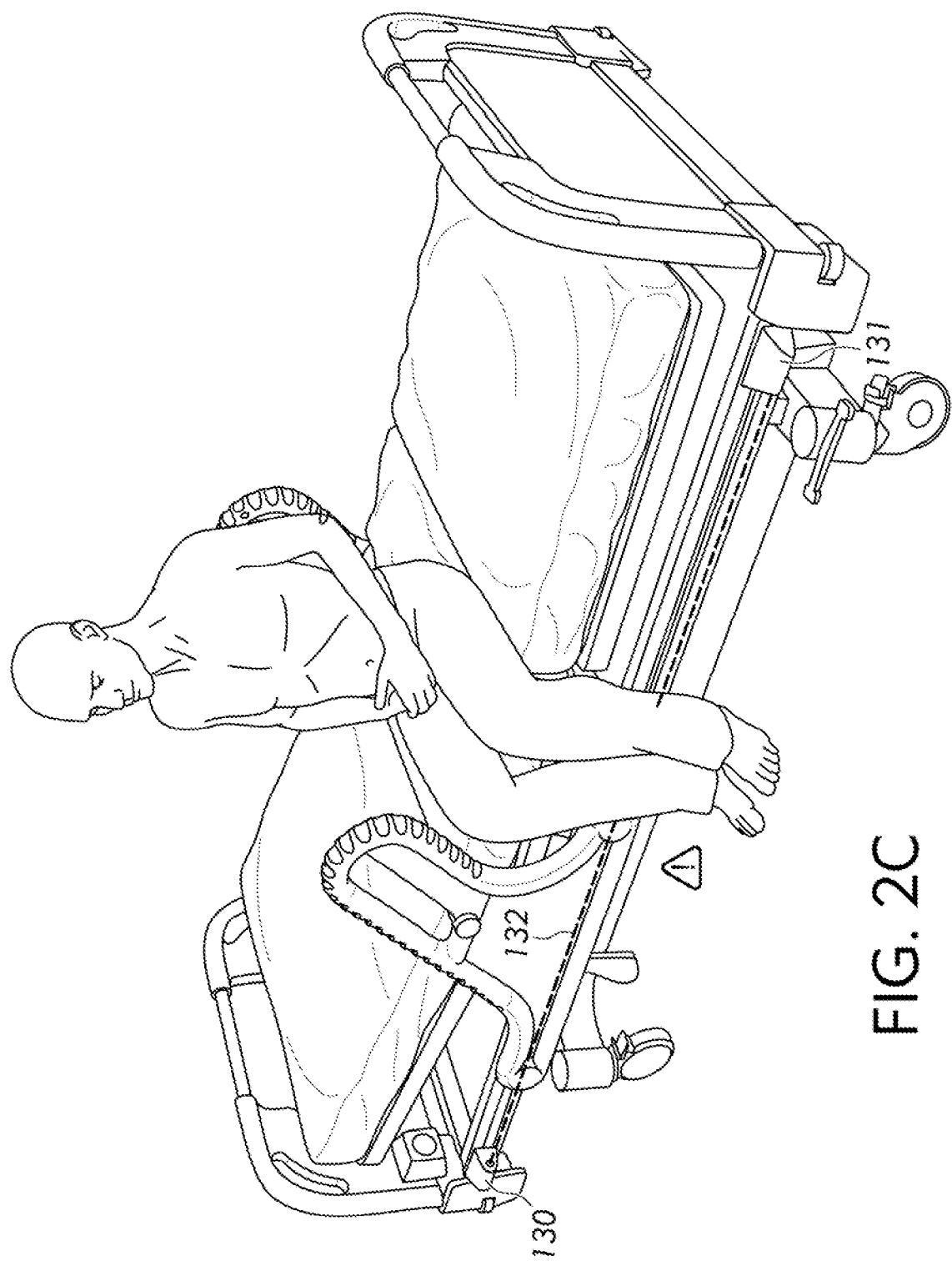
FIG. 2C shows the bedside handle system installed on the patient bed, showing patient sitting up on a side of the bed, according to various embodiments of the present disclosure.

FIG. 2C shows an example of the bedside handle system 100 installed on the patient bed 101, showing the patient sitting up on a side of the bed and interrupting second laser beam 132. The bedside handle system 100 thus sends an alert signal as described above, indicating among other details that the second laser beam 132 has been interrupted, e.g., that patient is about to stand up or has stood up out of the bed.

Figure 3A:
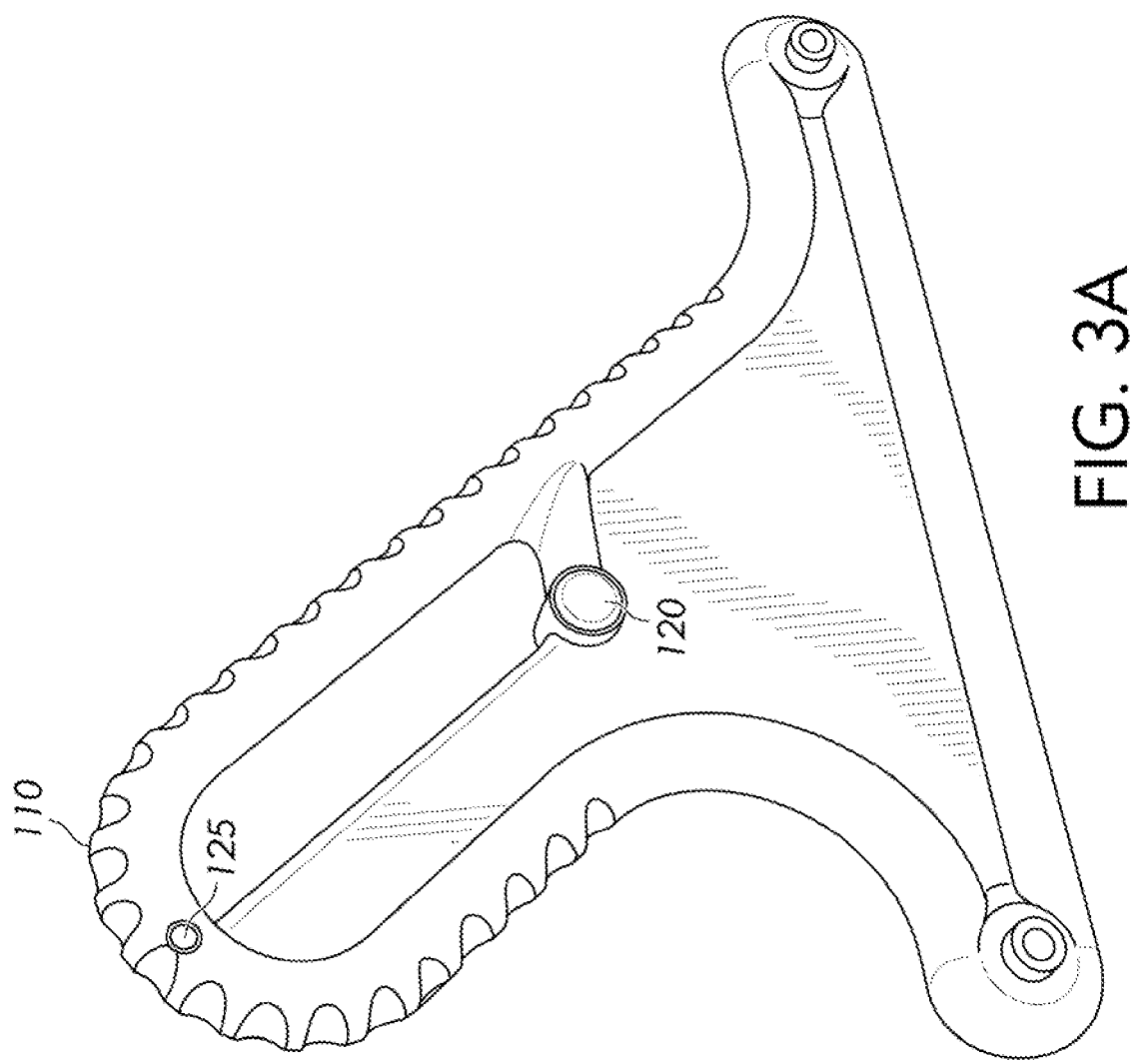
FIGS. 3A and 3B show an example of the handle of the bedside handle system, according to various embodiments of the present disclosure.
Figure 3B:
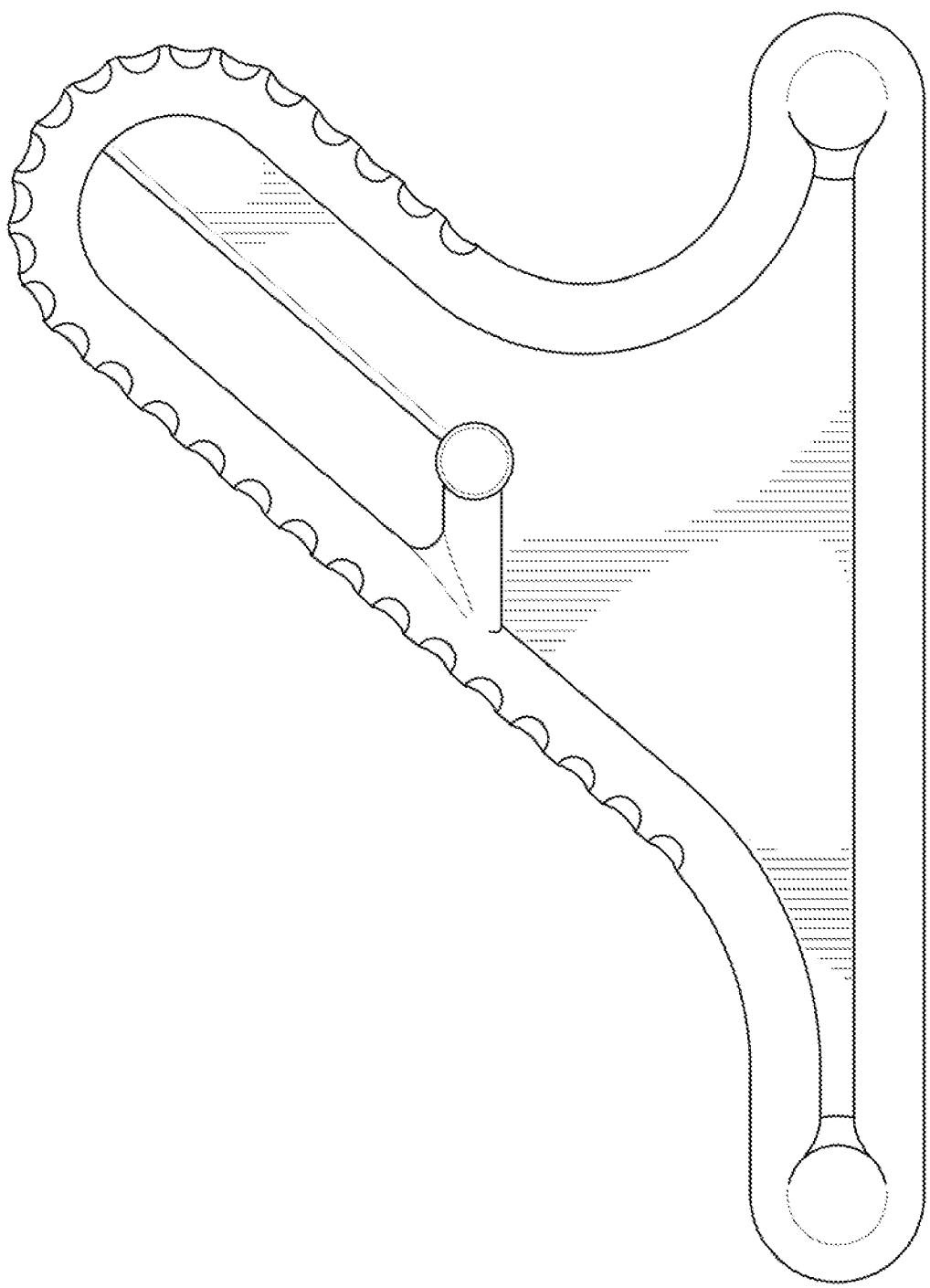

FIGS. 3A and 3B show an example of the handle 110 of the bedside handle system 100. Although the handles 110 and 111 have been shown to have triangular shape with a horizontal lower part and a diagonal leaning upper part, the handles 110 and 111 may have other suitable shape. In some embodiments, the shape and size of handles 110 and 111 may depend on the shape and size of the bed.

FIGS. 4A to 5B show an example of the parts of the handle 110 and 111. In some embodiments, the handle 110 and 111 may include an internal bracket 500 and a sleeve 400. The internal bracket may be made of pre-welded steel, or other suitable material. The sleeve may be made of pre-fabricated molded plastic, or other suitable material. The sleeve 400 may fixedly slide over bracket 500. Or the sleeve 400 may releasably slide over bracket 500 and secured to the bracket using suitable securing mechanism, e.g., screws, Velcro, adhesion, etc. The laser transmitter 124/receiver 125 may be fixedly attached to the sleeve.

Figure 6B:
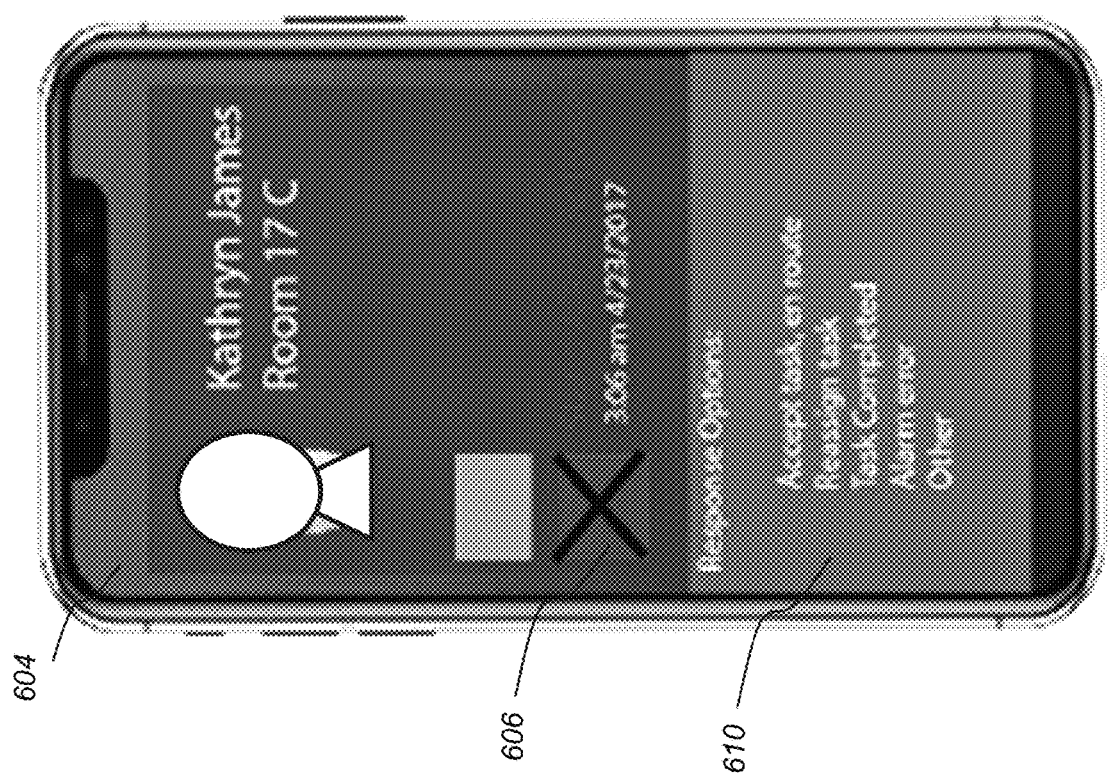
FIGS. 6A and 6B show example graphical user interfaces (GUIs) of alerts of the bedside handle system, according to various embodiments of the present disclosure.
Figure 6A:
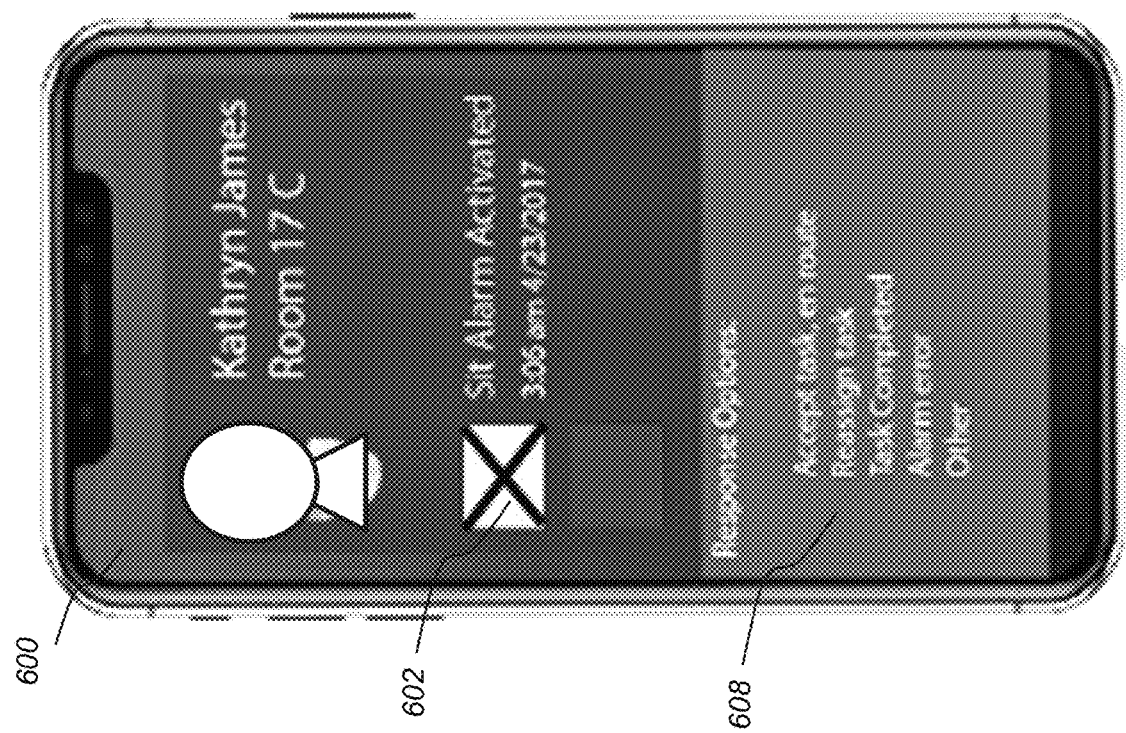

FIGS. 6A and 6B show example graphical user interfaces (GUIs) of alerts that the handle system 100 may send. For example, GUI 600 shows an alert (or alarm) that a "Sit Alarm" has been activated for patient "Kathryn James" in "Room 17C". This alert indicates that the patient has sat up on the bed. The alert may also include an easy-to-recognize color-coded icon 602. The GUI may also suggest/provide action options 608 for the attending nurse, for example, "Accept task, en route" (e.g., nurse accepts task and en route to check on patient), "Reassign task" (e.g., nurse reassigns and sends alert to another nurse), "Task completed" (e.g., nurse has checked on patient and completes necessary tasks), "Alarm error" (e.g., no laser beam interrupted), "Other" (further options for nurse to enter info), etc.

GUI 604 shows an alert (or alarm) that a "Stand Alarm" has been activated for patient "Kathryn James" in "Room 17C". This alert indicates that the patient has stood up or about to stand up out of the bed. The alert may also include an easy-to-recognize color-coded icon 606. The GUI may also suggest/provide action options 610 for the attending nurse, similar to options 608 as described above.

In some embodiments, when the provided App of the system 100 which runs on the remote device receives an alert, it may retrieve further information data, based on the alert, for display on the remote device. For example, the data may include detailed patient data.

Figure 7:
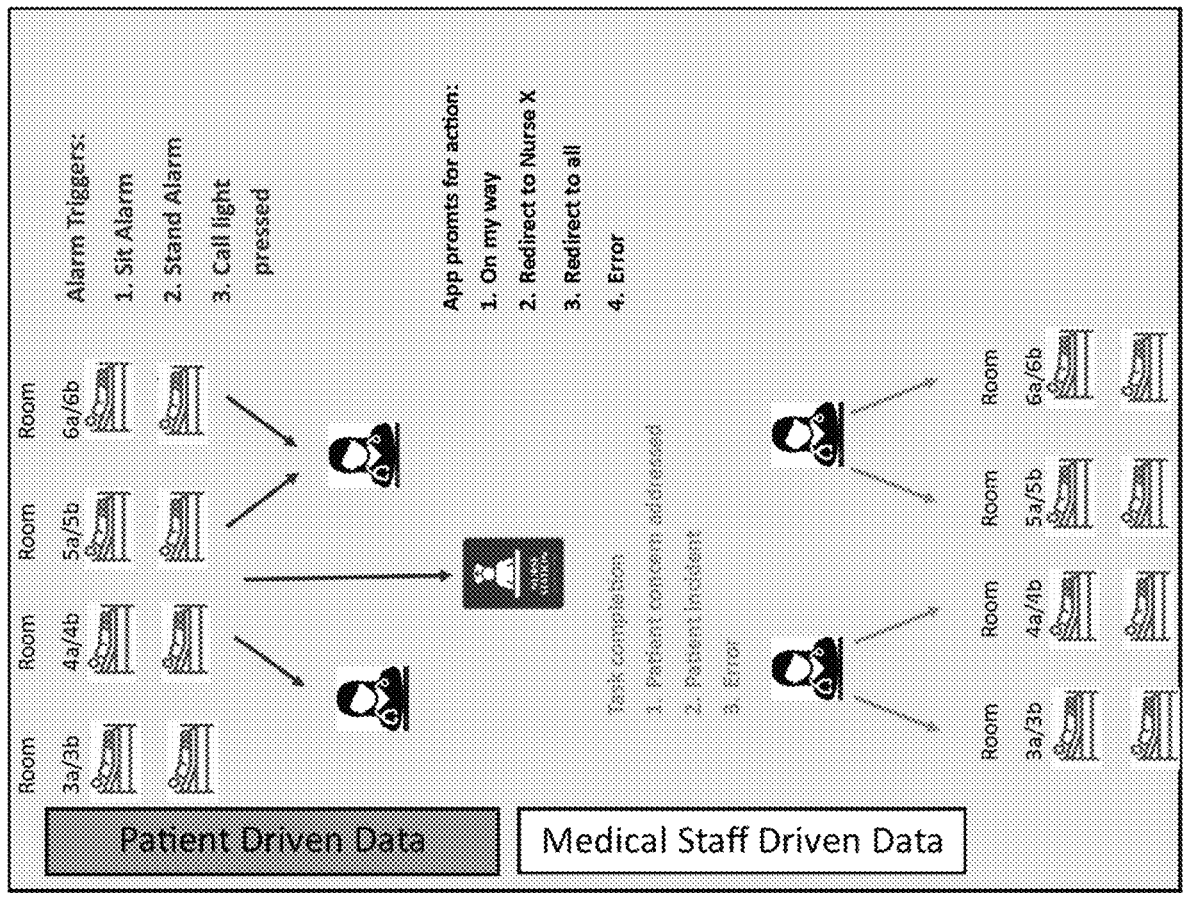
FIG. 7 shows an example overview data flow diagram of the handle of the bedside handle system, according to various embodiments of the present disclosure.

FIG. 7 shows an example overview data flow diagram 700 of the handle system 100. Although not shown, the system 100 may include a central control application that provides control and management functions, as well as providing a dashboard for displaying control and management functions, and historical and statistical data.

Assignment. In some embodiments, the App may allow for staff to activate the monitoring status of patients. For example, some patients may not need monitoring, some will need to be monitored only if standing, and others will need to be monitored for sitting and standing. Night/Day/24-hour options may also be available. The App may also allow the staff to designate if the alarm signals are to be transmitted to a nursing station, a specified caregiver/staff person, or both.

Status Update. In some embodiments, the App may provide function to update staff on the status of any given patient. The instant an alarm is signaled, the App may track the response time. Staff will then have the opportunity to very quickly and easily input a response as to what happened to that patient, and if appropriate, reset the alarm. The App also provides a section for notes and comments which will be attached to any given event.

Analytic. In some embodiments, the App may gather data that are extremely powerful and useful for facilities to better understand, and subsequently prevent patient falls, for example in the nursing home settings. Some benchmarks will include alarm response rates, individual staff time-to-patient data, specific station fall rates, specific shift fall rates, and facility-wide fall rates, among others. The App may also be compliant with the Health Insurance Portability and Accountability Act (HIPPA).

In some embodiments, the present disclosure may include a "Portable Laser Alerts" system that includes an adhesive laser transmitter and receiver which can easily be attached to each side of the wheelchair handles. When the wheelchair patient rises from the wheelchair, the laser will be triggered. The Wi-Fi transmitter can be strapped to the back of the chair. These portable laser alerts may tie into the system with the other alarms but will indicate the location (e.g., "main hallway", "PT room") rather than a room number.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

It is to be understood that this disclosure is not limited to the particular embodiments described herein, as such may, of course, vary. It is also to be understood that the terminology used herein is for the purpose of describing particular embodiments only and is not intended to be limiting.

As used herein and in the appended claims, the singular forms "a," "an," and "the" include plural referents unless the context clearly dictates otherwise.

In general, terms such as "coupled to," and "configured for coupling to," and "secure to," and "configured for securing to" and "in communication with" (for example, a first component is "coupled to" or "is configured for coupling to" or is "configured for securing to" or is "in communication with" a second component) are used herein to indicate a structural, functional, mechanical, electrical, signal, optical, magnetic, electromagnetic, ionic or fluidic relationship between two or more components or elements. As such, the fact that one component is said to be in communication with a second component is not intended to exclude the possibility that additional components may be present between, and/or operatively associated or engaged with, the first and second components.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

Various aspects have been presented in terms of systems and engines that may include several components, modules, and the like. It is to be understood and appreciated that the various systems and engines may include additional components, modules, etc. and/or may not include all the components, modules, etc. discussed in connection with the figures. A combination of these approaches may also be used. The various aspects and embodiments disclosed herein can be performed on electrical devices including devices that utilize touch screen display technologies and/or mouse-and-keyboard type interfaces. Examples of such devices include computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD), BluRay™ . . . ), smart cards, solid-state devices (SSDs), and flash memory devices (e.g., card, stick). Of course, those skilled in the art will recognize many modifications may be made to this configuration without departing from the scope of the disclosed aspects.

What is claimed is:

1. A bedside handle system having multiple-stage motion detection and wireless alert, the bedside handle system comprising:
   a first handle attached to a first side rail of a patient bed, the first handle comprises a first laser beam transmitter configured to transmit a first laser beam;
   a second handle attached to a second side rail of the patient bed, the second handle comprises a first laser beam receiver configured to receive the first laser beam;
   a second laser beam transmitter attached to a first side of the patient bed and configured to transmit a second laser beam;
   a second laser beam receiver attached to the first side of the patient bed and configured to receive the second laser beam;
   a third laser beam transmitter attached to a second side of the patient bed and configured to transmit a third laser beam;
   a third laser beam receiver attached to the second side of the patient bed and configured to receive the third laser beam;
   a first call button built into the first handle;
   a wireless communication device attached to the patient bed and configured to receive signal from the first, second and third laser beam receivers; and
   wherein the wireless communication device is further configured to transmit an alert signal when one of the first laser beam, the second laser beam and the third laser beam is interrupted.

2. The bedside handle system of claim 1, wherein the first laser beam transmitter is positioned near a top end of the first handle, and the first laser beam receiver is positioned near a top end of the second handle.

3. The bedside handle system of claim 1, wherein the second laser beam transmitter is positioned near a foot of the patient bed, and the second laser beam receiver is positioned near a head of the patient bed.

4. The bedside handle system of claim 1, wherein the third laser beam transmitter is positioned near a foot of the patient bed, and the third laser beam receiver is positioned near a head of the patient bed.

5. The bedside handle system of claim 1 further comprises a second call button built into the second handle.

6. The bedside handle system of claim 1, wherein the first, second third laser beams are not human perceivable.

7. The bedside handle system of claim 1, wherein the wireless communication device supports Wi-Fi technology.

8. The bedside handle system of claim 1, wherein the wireless communication device transmits the alert signal in a form of one or more messages to one or more remote devices.

9. The bedside handle system of claim 1 further comprises a two-way communication device having at least a speaker, a microphone and a video display screen.

10. The bedside handle system of claim 1, wherein the first handle and the second handle each comprises a steel bracket and a molded plastic sleeve.

11. The bedside handle system of claim 1 further comprises a software application configured to receive the alert signal and provide signal details for display on a display screen.

12. The bedside handle system of claim 11, wherein the software application retrieves data, based on the alert signal, for display on the display screen.

* * * * *